United States Patent
Hashimoto et al.

(10) Patent No.: US 10,070,840 B2
(45) Date of Patent: Sep. 11, 2018

(54) X-RAY COMPUTED TOMOGRAPHY APPARATUS AND RADIATION MEDICAL IMAGING DIAGNOSTIC APPARATUS

(71) Applicant: Toshiba Medical Systems Corporation, Otawara-shi (JP)

(72) Inventors: Atsushi Hashimoto, Otawara (JP); Shuya Nambu, Nasushiobara (JP); Takaya Umehara, Kawasaki (JP); Akira Nishijima, Nasushiobara (JP); Koichi Miyama, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 184 days.

(21) Appl. No.: 15/164,139

(22) Filed: May 25, 2016

(65) Prior Publication Data
US 2017/0095222 A1    Apr. 6, 2017

(30) Foreign Application Priority Data

Oct. 2, 2015  (JP) .................................. 2015-196391

(51) Int. Cl.
*A61B 6/00*  (2006.01)
*A61B 6/03*  (2006.01)

(52) U.S. Cl.
CPC ............ *A61B 6/5258* (2013.01); *A61B 6/032* (2013.01)

(58) Field of Classification Search
CPC ....... A61B 6/032; A61B 6/5258; A61B 6/585; H04N 5/357; H04N 5/361
See application file for complete search history.

(56) References Cited

U.S. PATENT DOCUMENTS

| | | | | |
|---|---|---|---|---|
| 5,923,722 A * | 7/1999 | Schulz | ................... | G01N 23/04 |
| | | | | 378/98.7 |
| 2004/0096036 A1* | 5/2004 | Yanoff | ................. | A61B 6/5235 |
| | | | | 378/98.8 |
| 2005/0151086 A1* | 7/2005 | Spahn | ................... | A61B 6/583 |
| | | | | 250/370.08 |
| 2009/0080595 A1* | 3/2009 | Nishii | .................... | A61B 6/032 |
| | | | | 378/4 |
| 2010/0020933 A1* | 1/2010 | Topfer | ...................... | G06T 5/50 |
| | | | | 378/98.11 |

FOREIGN PATENT DOCUMENTS

| | | |
|---|---|---|
| JP | 8-243100 | 9/1996 |
| JP | 2005-230536 | 9/2005 |
| JP | 5182371 | 4/2013 |
| WO | WO 2010/004776 A1 | 1/2010 |

* cited by examiner

*Primary Examiner* — Glen Kao
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, X-ray detector, data acquisition circuit, and correction circuit. The X-ray tube generates X-rays. The X-ray detector detects the X-rays. The data acquisition circuit acquires data corresponding to an output from the X-ray detector. The correction circuit executes correction processing for third data acquired by the data acquisition circuit in actual scanning, based on first data acquired by the data acquisition circuit in a state of non-irradiation with X-rays before the actual scanning and second data acquired by the data acquisition circuit in the state of non-irradiation with X-rays after the actual scanning.

10 Claims, 11 Drawing Sheets

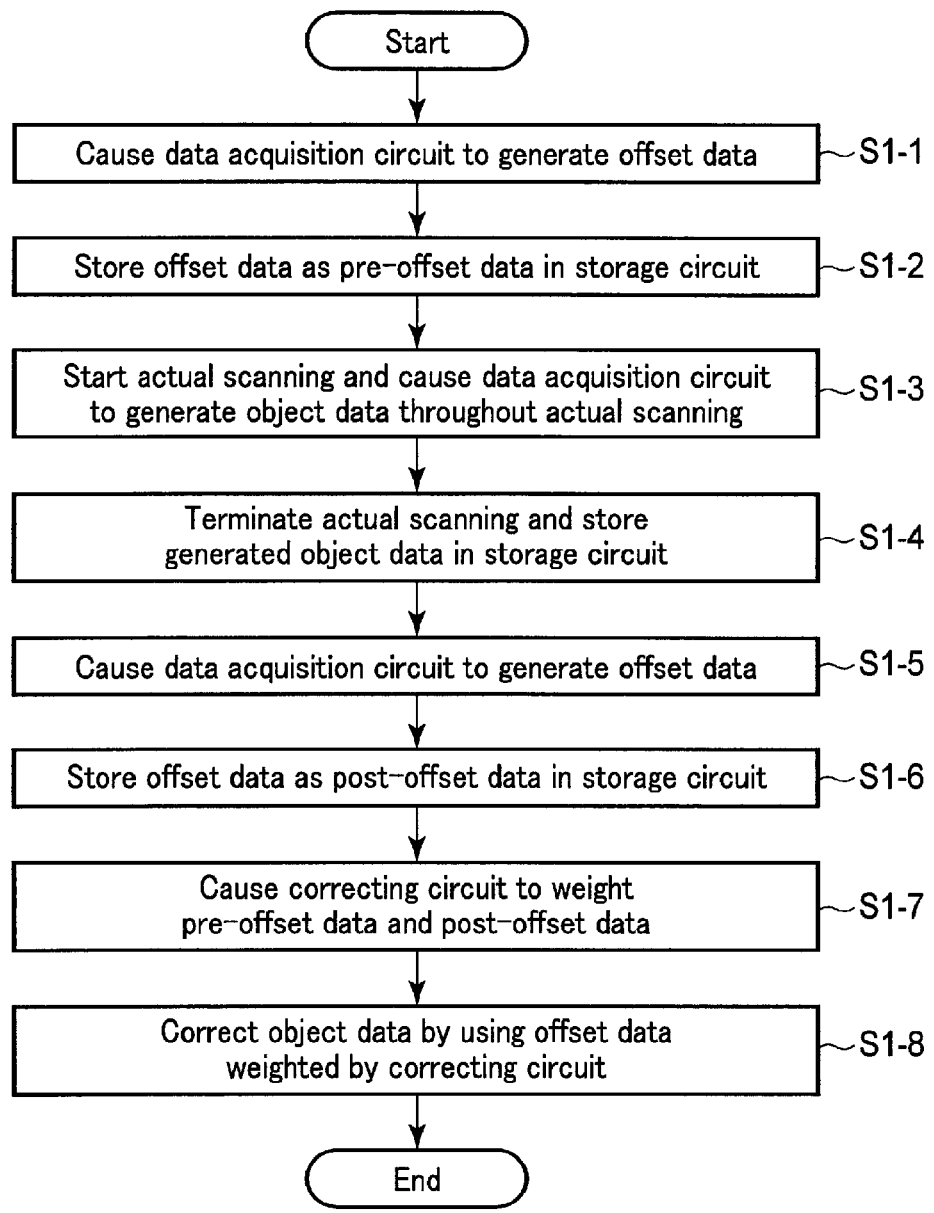
F I G. 3

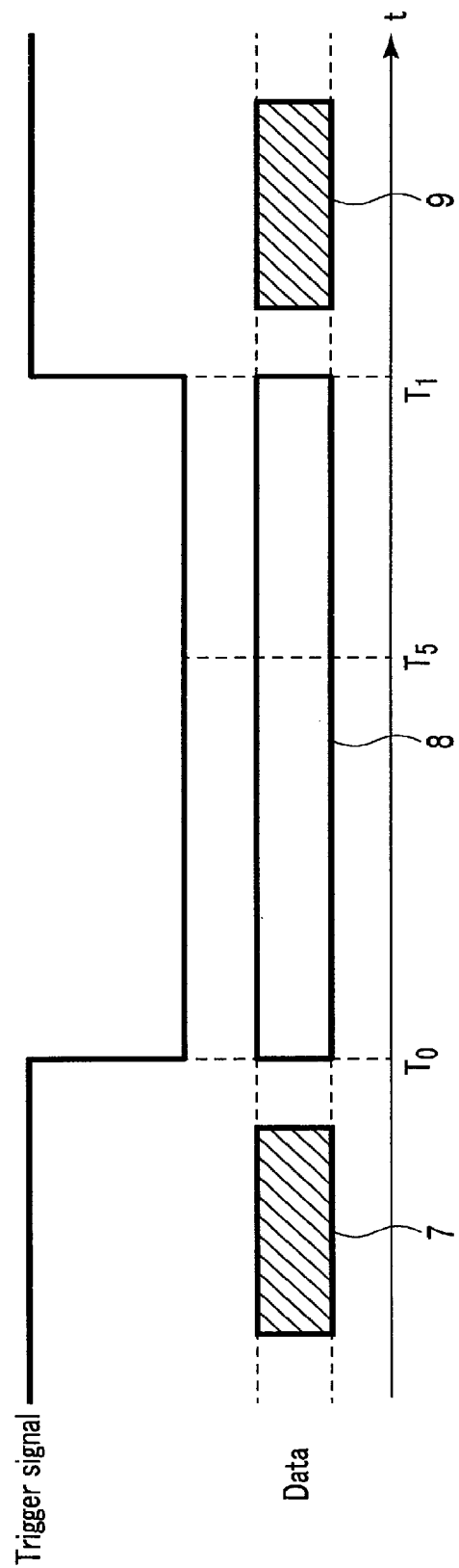
F I G. 6A

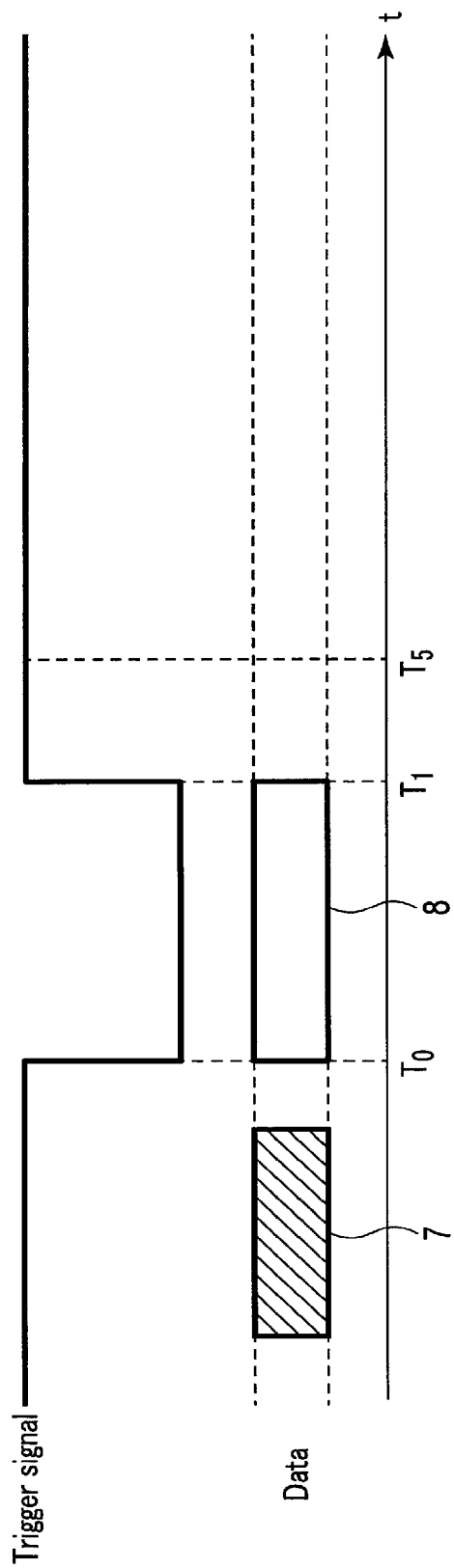
F I G. 6B

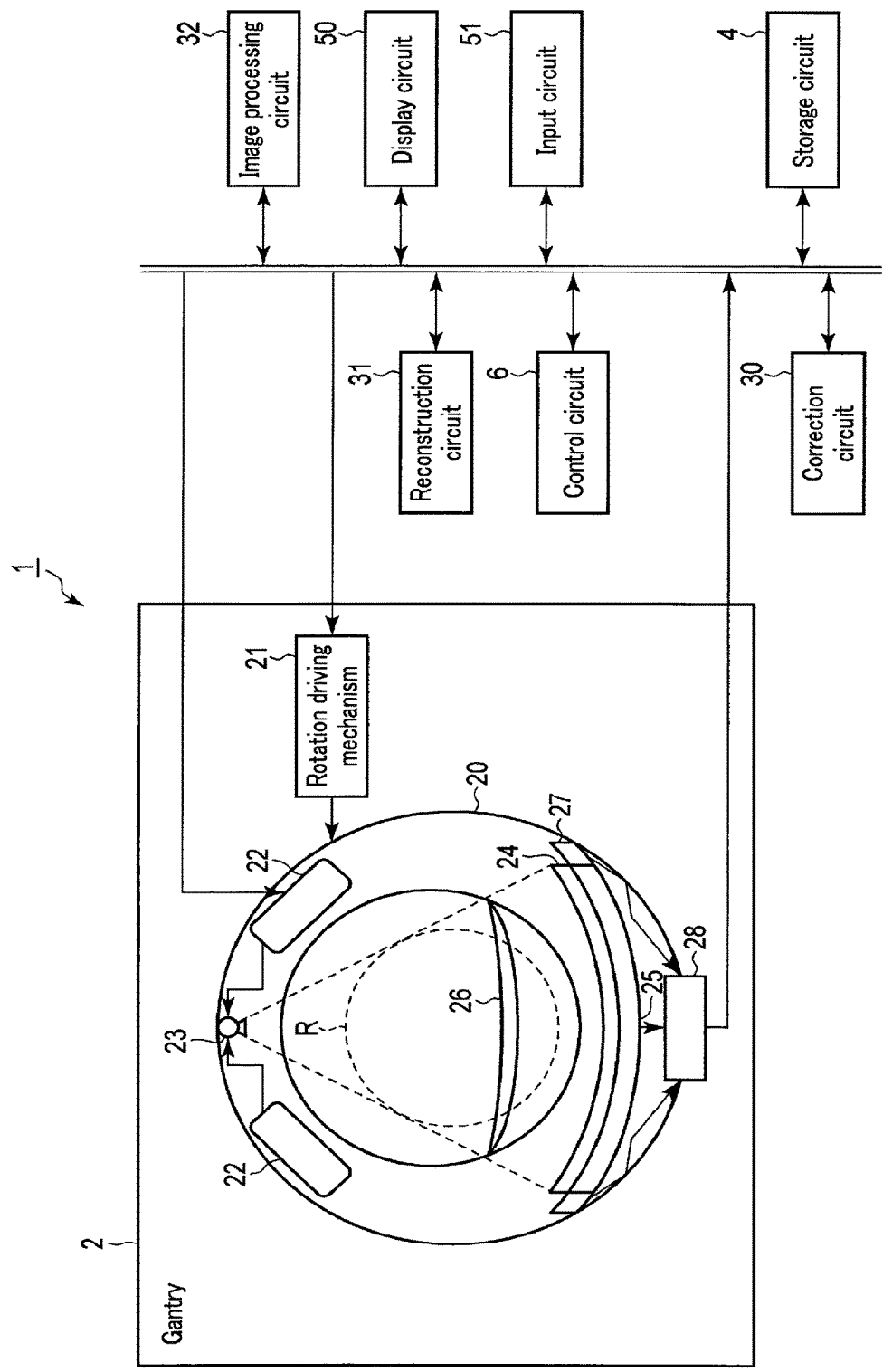
F I G. 8

X-RAY COMPUTED TOMOGRAPHY APPARATUS AND RADIATION MEDICAL IMAGING DIAGNOSTIC APPARATUS

CROSS-REFERENCE TO RELATED APPLICATIONS

This application is based upon and claims the benefit of priority from the prior Japanese Patent Application No. 2015-196391, filed Oct. 2, 2015, the entire contents of which are incorporated herein by reference.

FIELD

Embodiments described herein relate generally to a radiation medical imaging diagnostic apparatus typified by an X-ray computed tomography apparatus, an X-ray diagnostic apparatus, a single photon emission computed tomography apparatus, a positron radiation computed tomography apparatus, and the like.

BACKGROUND

When making diagnoses of the insides of objects, doctors and the like widely use a radiation medical imaging diagnostic apparatus typified by an X-ray computed tomography (X-ray CT) apparatus, an X-ray diagnostic apparatus, a single photon emission tomography (SPECT) apparatus, a positron tomography (PET) apparatus, and the like. Assume that the following description including that of the embodiments will exemplify an X-ray computed tomography apparatus.

Before executing object scanning (actual scanning), that is, irradiating an object with X-rays, an X-ray computed tomography apparatus executes correction (calibration) by using offset data acquired by a DAS (Data Acquisition System) in a state of no irradiation with X-rays.

With the lapse of a predetermined time, however, offset data acquired in advance deviates from offset data included in data obtained by actual scanning (offset drift). This causes artifacts. For this reason, a general X-ray computed tomography apparatus obtains offset data again when a predetermined time elapses, and executes correction by using the offset data obtained again.

When performing scanning accompanied by long-time imaging without allowing to use any quiescent time, such as shuttle helical scanning, it is impossible to properly obtain offset data again, resulting in the difficulty in suppressing artifacts.

BRIEF DESCRIPTION OF THE DRAWINGS

FIG. 3 is a flowchart showing Example 1 in the X-ray computed tomography apparatus according to the embodiment;

FIG. 6A is a diagram showing Example 3 in the X-ray computed tomography apparatus according to the embodiment;

FIG. 6B is a diagram showing Example 3 in the X-ray computed tomography apparatus according to the embodiment;

FIG. 8 is a block diagram showing an example of the arrangement of the X-ray computed tomography apparatus according to Example 4;

DETAILED DESCRIPTION

In general, according to one embodiment, an X-ray computed tomography apparatus includes an X-ray tube, an X-ray detector, a data acquisition circuit, and a correction circuit. The X-ray tube generates X-rays. The X-ray detector detects the X-rays. The data acquisition circuit acquires data corresponding to an output from the X-ray detector. The correction circuit executes correction processing for third data acquired by the data acquisition circuit in actual scanning, based on first data acquired by the data acquisition circuit in a state of non-irradiation with X-rays before the actual scanning and second data acquired by the data acquisition circuit in the state of non-irradiation with X-rays after the actual scanning.

The embodiment will be described below with reference to the accompanying drawing.

Figure 1:
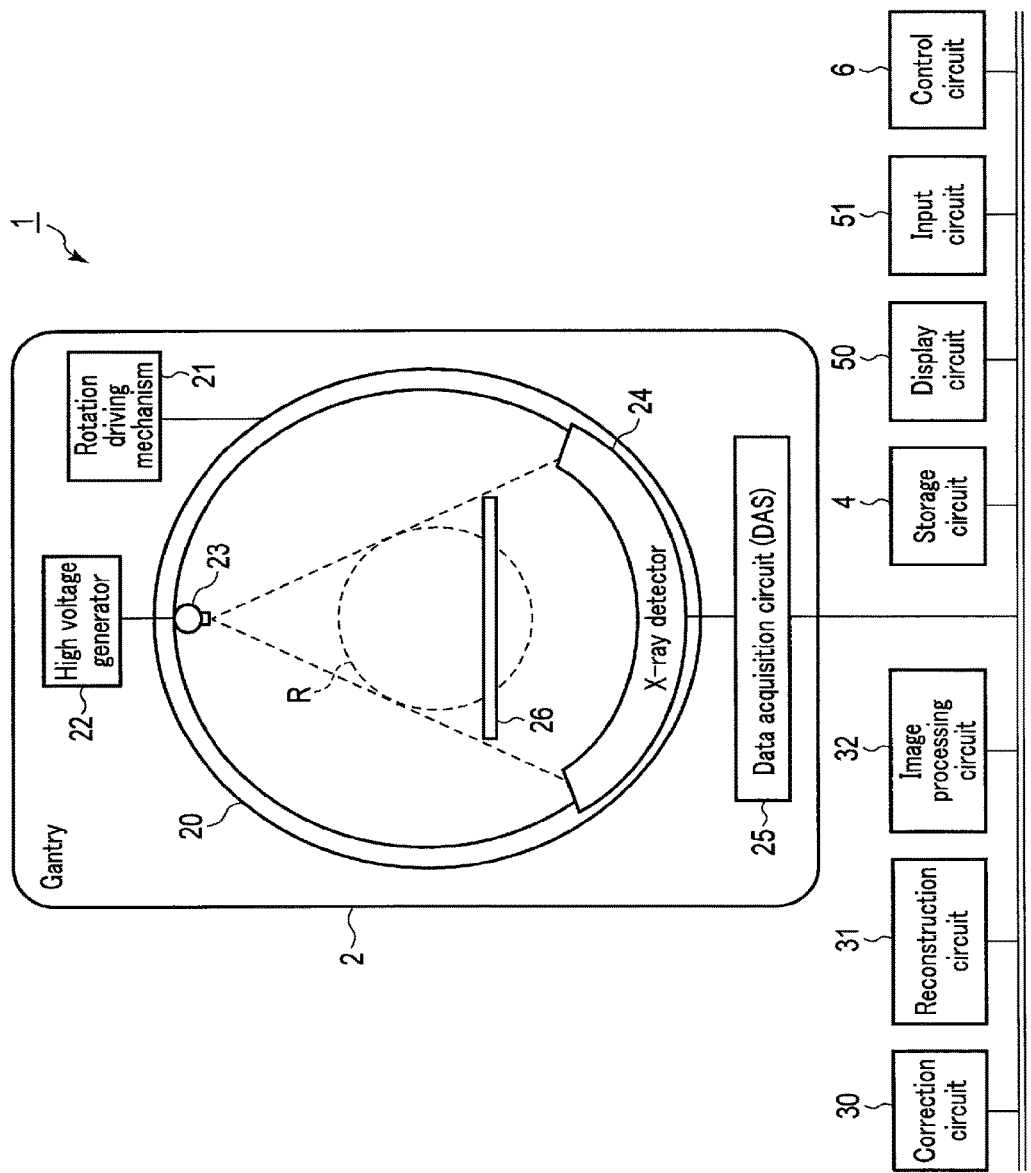
FIG. 1 is a block diagram showing the arrangement of an X-ray computed tomography apparatus according to an embodiment.

FIG. 1 is a block diagram showing an X-ray computed tomography apparatus 1 according to the embodiment.

X-ray computed tomography apparatuses include various types of apparatuses, e.g., a rotate/rotate-type apparatus in which an X-ray tube and an X-ray detector rotate together around an object and a stationary/rotate-type apparatus in which many X-ray detection elements arrayed in the form of a ring are fixed, and only an X-ray tube rotates around an object. Either type can be applied to the X-ray computed tomography apparatus 1 according to this embodiment. In order to reconstruct a medical image, data corresponding to one rotation around an object, i.e., 360°, is required, or (180°+fan angle) data is required in the half scan method. Either reconstruction scheme can be applied to the X-ray computed tomography apparatus 1 according to the embodiment. As mechanisms of converting incident X-rays into charge, the following techniques are the mainstream: an indirect conversion type that converts X-rays into light through a phosphor such as a scintillator and converts the light into charge through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of these schemes can be used.

Recently, with advances toward the commercialization of a so-called multi-tube type X-ray computed tomography apparatus having a plurality of pairs of X-ray tubes and X-ray detectors mounted on a rotating ring, related techniques have been developed. The X-ray computed tomography apparatus 1 according to the embodiment may be a conventional single-tube type X-ray computed tomography apparatus or a multi-tube type X-ray computed tomography apparatus. The single-tube type X-ray computed tomography apparatus will be exemplified here. In addition, the X-ray computed tomography apparatus 1 according to the embodiment may be an energy integration type X-ray computed tomography apparatus or a photon counting type X-ray computed tomography apparatus capable of energy discrimination.

As shown in FIG. 1, the X-ray computed tomography apparatus 1 according to the embodiment includes a gantry 2, a correction circuit 30 (processing unit), a reconstruction circuit 31, an image processing circuit 32, a storage circuit 4, a display circuit 50, an input circuit 51, and a control circuit 6 (control unit).

The gantry 2 includes a rotating frame 20, a rotation driving mechanism 21, a high voltage generator 22, an X-ray tube 23, an X-ray detector 24, and a data acquisition circuit 25 (data acquisition unit).

The rotating frame 20 and the rotation driving mechanism 21 constitute a rotating support mechanism (not shown). In other words, the rotating support mechanism is constituted by the rotating frame 20, a frame support mechanism (not shown) which supports the rotating frame 20 so as to make it rotatable about a rotation axis Z, and the rotation driving mechanism 21 which drives the rotation of the rotating frame 20.

The high voltage generator 22 is arranged on the rotating frame 20. The high voltage generator 22 generates a high voltage (tube voltage) to be applied to the X-ray tube 23 and a current (tube current or filament current) to be supplied to the X-ray tube 23. The high voltage generator 22 generates a tube voltage and a tube current in accordance with control signals input from the control circuit 6 (to be described later) via a slip ring (not shown).

Upon receiving a tube voltage and a tube current from the high voltage generator 22, the X-ray tube 23 emits X-rays from an X-ray focus. The X-ray tube 23 generates multicolor X-rays. Multicolor X-rays are constituted by monochromatic X-rays having different energies.

The X-ray detector 24 is arranged at a predetermined position on the rotating frame 20 at a position and an angle to face the X-ray tube 23 through the rotation axis Z. The X-ray detector 24 includes a plurality of X-ray detection elements. Assume that in the following description, a single X-ray detection element forms a single channel. A plurality of channels are two-dimensionally arranged in two directions, i.e., the slice direction and the arc direction (channel direction) which is perpendicular to the rotation axis Z and whose radius corresponds to the distance from an X-ray focus, as a center, from which X-rays emerge, to the center of the light-receiving portion of an X-ray detection element corresponding to one channel. The two-dimensional array is formed by arranging a plurality of channels, one-dimensionally arrayed along the channel direction, in the form of a plurality of columns arranged in the slice direction. The X-ray detector 24 having such two-dimensional array of X-ray detection elements may be formed by arranging a plurality of modules, one-dimensionally arrayed in a nearly arc direction, in the form of a plurality of columns in the slice direction. In addition, the X-ray detector 24 may be constituted by a plurality of modules each having a plurality of X-ray detection elements arrayed in one column. In this case, the respective modules are one-dimensionally arrayed in the nearly arc direction along the above channel direction.

When performing imaging or scanning, an object is placed on a top 26 and inserted into a cylindrical imaging region R between the X-ray tube 23 and the X-ray detector 24. The data acquisition circuit 25 is connected to the output of the X-ray detector 24.

The data acquisition circuit 25 is mounted on the rotating frame 20. The data acquisition circuit 25 includes an I-V converter (not shown) which converts a current signal from each channel of the X-ray detector 24 into a voltage, an integrator (not shown) which periodically integrates this voltage signal in synchronism with the irradiation period of X-rays, an amplifier (not shown) which amplifies an output signal from the integrator, and an ADC (Analog to Digital Converter) which converts an output signal from the amplifier into a digital signal. The data acquisition circuit 25 acquires (generates) data based on outputs from the X-ray detector 24.

More specifically, the data acquisition circuit 25 generates data for each of a plurality of channels in association with data (view angle data) representing a view angle at the time of point of acquisition of the data. This data is a set of data values corresponding to outputs from the X-ray detector 24. For the sake of descriptive convenience, a set of data acquired at the same time with one shot at the same view angle throughout all the channels will be referred to as a data set. The respective view angles are represented by angles in the range of 0° to 360° which represent the respective positions on a circular orbit centered on the rotation axis Z, along which the X-ray tube 23 revolves, with the angle of the uppermost portion on the circular orbit in an upward vertical direction from the rotation axis Z being 0°. Note that a data value of a data set which corresponds to each channel is identified by the number of rotations of the rotating frame 20, a view angle, a cone angle, and a channel number.

That is, the data acquisition circuit 25 generates a data set based on outputs from the X-ray detector 24. The data acquisition circuit 25 periodically generates a plurality of data sets in accordance with the rotation of the rotating frame 20. Assume that in this case, a plurality of periodically generated data sets indicate a plurality of data sets generated at the same view angle with different numbers of rotations of the rotating frame 20 in accordance with the rotation of the rotating frame 20 around the rotation axis Z. The plurality of data sets generated by the data acquisition circuit 25 are transmitted to and stored in the storage circuit 4 (to be described later) via a noncontact data transmission device and a bus (neither of which is shown).

Note that the X-ray detector 24 and the data acquisition circuit 25 generate dark currents due to the influences of semiconductor characteristics, Joule heat, and the like regardless of whether the X-ray detector 24 performs X-ray detection. The dark currents are a cause of noise in the process of generating volume data from data in the reconstruction circuit 31 (to be described later). In addition, a tomographic image generated by the image processing circuit 32 (to be described later) based on volume data having noise has artifacts or a low resolution.

In other words, the data acquisition circuit 25 can generate data originating from the above dark currents at a timing when an object is not irradiated with X-rays. Assume that in this embodiment, data concerning imaging of an object (in a state of irradiation with X-rays) is called "object data (set)" and data originating from dark currents (in a state of no irradiation with X-rays) is called "offset data (set)" so as to be discriminated from each other. In this case, an offset data set is preferably held for each view. In this case, all offset data concerning one view may be held, or offset data (average value) obtained by averaging all offset data concerning one view may be held.

The correction circuit 30 corrects (calibrates) an object data set stored in the storage circuit 4, generated by the data acquisition circuit 25, by using an offset data set stored in the storage circuit 4, generated by the data acquisition circuit 25. This correction is to, for example, subtract an offset data set from an object data set for each channel.

In the X-ray computed tomography apparatus 1 according to this embodiment, in particular, the correction circuit 30 corrects the object data set (third data) based on pre-offset data (first data) generated before the generation of an object data set and post-offset data (second data) generated after the generation of the object data set. This correcting function will be referred to as a "multi-offset correcting function". The correction circuit 30 executes correction concerning various types of preprocessing such as logarithmic conversion and X-ray intensity correction with respect to object data corrected by the multi-offset function. The object data (projection data) corrected by the correction circuit 30 is output to the reconstruction circuit 31, the storage circuit 4, and the like.

The reconstruction circuit 31 reconstructs an almost columnar three-dimensional image (volume data), based on an object data set corrected by the correction circuit 30, which is a data set falling within the view angle range of 360° or 180°+fan angle, by the Feldkamp method or cone beam reconstruction method. The reconstruction circuit 31 reconstructs two-dimensional images (tomographic images) by, for example, the fan beam reconstruction method (fan beam convolution back projection method) or the filtered back projection method.

The Feldkamp method is a reconstruction method to be used when projection rays intersect a reconstruction plane like a cone beam. The Feldkamp method is an approximate image reconstruction method of performing processing by regarding a projection beam as a fan projection beam in convolution on the premise that the cone angle is small, whereas back projection processing is an approximate image reconstruction method performed along a ray in scanning operation. The cone beam reconstruction method is a reconstruction method which corrects data in accordance with the angle of a ray relative to a reconstruction plane as a method which can suppress cone angle errors more than the Feldkamp method.

The image processing circuit 32 generates a medical image of an arbitrary slice based on volume data reconstructed by the reconstruction circuit 31.

The storage circuit 4 stores image data such as data (offset data and object data) acquired by the data acquisition circuit 25, volume data reconstructed by the reconstruction circuit 31, tomographic images generated by the image processing circuit 32, and medical images of arbitrary slices. The storage circuit 4 also stores programs and the like concerning the respective types of control performed by the X-ray computed tomography apparatus 1.

The storage circuit 4 is implemented as a storage device such as an HDD (Hard Disk Drive) or SSD (Solid State Drive). The storage circuit 4 can also be implemented as a memory such as a RAM (Random Access Memory) which stores information (e.g., arguments, arrays, structures, and memory addresses) temporarily required for program arithmetic operations.

The display circuit 50 displays, for example, a screen of a GUI (Graphic User Interface). The display circuit 50 displays medical images reconstructed by the reconstruction circuit 31, conditions set for X-ray computed tomography, and the like via the screen of the graphical user interface. That is, the display circuit 50 is implemented as a monitor such as a CRT display, liquid crystal display, organic EL display, or plasma display.

The input circuit 51 accepts operations/inputs from an operator such as a doctor who uses the X-ray computed tomography apparatus 1 according to this embodiment. The control circuit 6 (to be described later) executes predetermined processing based on operations/inputs accepted by the input circuit. Predetermined processing includes, for example, setting a scan sequence and setting an ROI (Region Of Interest). However, this is merely an example and not exhaustive. The input circuit 51 may be implemented as a keyboard, mouse, touch panel (electromagnetic induction scheme, magnetostriction scheme, or pressure-sensitive scheme), magnetic reader, or optical sensor.

The control circuit 6 functions as the main unit of the X-ray computed tomography apparatus 1 according to this embodiment. In other words, the control circuit 6 controls the operations of the respective constituent elements (e.g., the correction circuit 30, the reconstruction circuit 31, and the image processing circuit 32) of the X-ray computed tomography apparatus 1. More specifically, the control circuit 6 controls the high voltage generator 22, the gantry 2, and the like for X-ray computed tomography. Alternatively, the control circuit 6 controls the X-ray tube 23 and the data acquisition circuit 25 so as to execute a scan sequence of sequentially obtaining pre-offset data (first data) without the generation of X-rays, object data (third data) with the generation of X-rays, and post-offset data (second data) without the generation of X-rays.

That is, the control circuit 6 includes, for example, a CPU (Central Processing Unit) (not shown). The control circuit 6 executes various functions of the X-ray computed tomography apparatus 1 by reading out predetermined programs stored in the storage circuit 4.

Although FIG. 1 shows the control circuit 6 as a single circuit, the control circuit 6 may be practically implemented as the single circuit 6 or may be implemented so as to make the respective functions have control circuits 6. Alternatively, the control circuit 6 may be implemented as a combination of these forms. In addition, the control circuit 6 preferably has a memory (not shown) independently of the storage circuit 4.

Note that the X-ray computed tomography apparatus 1 according to this embodiment may be implemented as having an interface circuit (not shown). This interface circuit connects, for example, the X-ray computed tomography apparatus 1 to a telecommunication line (intranet or Internet). A radiology department information management system (not shown), a hospital information system (not shown), and the like are connected to this telecommunication line.

EXAMPLE 1

Example 1 concerning the multi-offset correcting function of the X-ray computed tomography apparatus 1 according to the embodiment will be described below.

Figure 2:
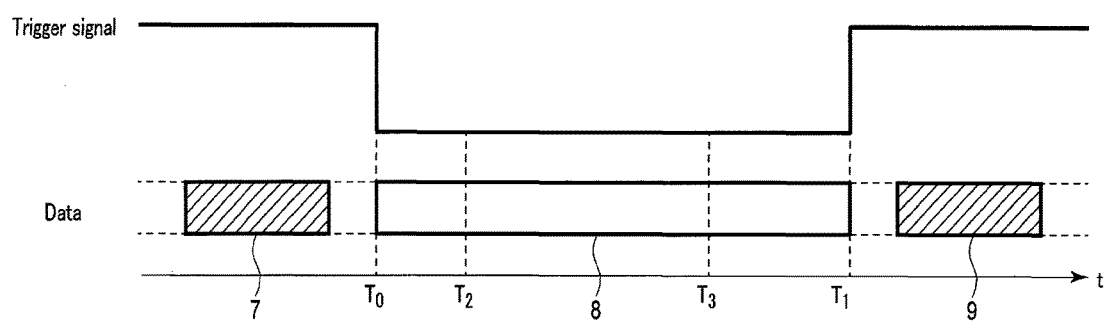
FIG. 2 is a diagram showing Example 1 in the X-ray computed tomography apparatus according to the embodiment.

FIG. 2 is a diagram (a graph representing temporal changes in various types of values/time series) showing Example 1 in the X-ray computed tomography apparatus 1 according to the embodiment.

The abscissa represents time t. FIG. 2 shows times $T_0$, $T_1$, $T_2$, and $T_3$.

A trigger signal is a signal for controlling irradiation with X-rays from the X-ray tube 23, and has two values, i.e., High and Low. When the value of a trigger signal is High (to be written as trigger signal=High hereinafter), the X-ray tube 23 emits no X-rays (stops emitting X-rays). In contrast to this, when the value of a trigger signal is Low (to be written as trigger signal=Low hereinafter), the X-ray tube 23 emits X-rays. Referring to FIG. 2, at time $T_0$, switching occurs from trigger signal=High to trigger signal=Low. In addition, at time $T_1$, switching occurs from trigger signal=Low to trigger signal=High. In accordance with a change in trigger signal=High/Low, whether to emit X-rays is decided.

Each data field indicates that the corresponding data is either offset data or object data by using a rectangle. A hatched rectangle indicates offset data generated in a state of no irradiation with X-rays. A rectangle without hatching indicates object data generated in a state of irradiation with X-rays. FIG. 2 shows pre-offset data 7, object data 8, and post-offset data 9.

FIG. 3 is a flowchart showing Example 1 in the X-ray computed tomography apparatus 1 according to the embodiment. Example 1 will be described below in accordance with each step in the flowchart of FIG. 3.

(Step S1-1)

Before the execution of actual scanning (that is, $t<T_0$), the data acquisition circuit 25 generates offset data as data originating from dark currents in a period during which the X-ray tube 23 emits no X-rays (proceeding to step S1-2).

(Step S1-2)

The offset data generated in step S1-1 is stored as the pre-offset data 7 in the storage circuit 4 (proceeding to step S1-3).

(Step S1-3)

When the X-ray tube 23 starts emitting X-rays upon switching from trigger signal=High to trigger signal=Low at $t=T_0$, actual scanning starts. The data acquisition circuit 25 generates object data throughout the actual scanning (proceeding to step S1-4).

(Step S1-4)

When the X-ray tube 23 stops emitting X-rays upon switching from trigger signal=Low to trigger signal=High at $t=T_1$, the actual scanning ends. The generated object data is stored as the object data 8 in the storage circuit 4 (step S1-5).

(Step S1-5)

The data acquisition circuit 25 generates offset data again as data originating from dark currents in a period during which the X-ray tube 23 emits no X-rays after the execution of the actual scanning (i.e., $t>T_1$) (proceeding to step S1-6).

(Step S1-6)

The offset data generated in step S1-5 is stored as the post-offset data 9 in the storage circuit 4 (proceeding to step S1-7).

(Step S1-7)

The correction circuit 30 assigns weights to the pre-offset data 7 and the post-offset data 9 in accordance with the ratio of the elapsed time of object scanning to the total time of the object scanning and the ratio of the remaining time of the object scanning to the total time of the object scanning (proceeding to step S1-8).

(Step S1-8)

The correction circuit 30 corrects the object data 8 by using the weighted pre- and post-offset data (the pre-offset data 7 and the post-offset data 9) (the procedure end).

In steps S1-7 and S1-8, for example, at time $T_2$ in FIG. 2, the correction circuit 30 weights the pre-offset data 7 by multiplying it by $(T_2-T_0)/(T_1-T_0)$, and weights the post-offset data 9 by multiplying it by $(T_1-T_2)/(T_1-T_0)$. The correction circuit 30 corrects the object data 8 by using the weighted pre- and post-offset data (the pre-offset data 7 and the post-offset data 9).

In steps S1-7 and S1-8, for example, at time $T_3$ in FIG. 2, the correction circuit 30 weights the pre-offset data 7 by multiplying it by $(T_3-T_0)/(T_1-T_0)$, and weights the post-offset data 9 by multiplying it by $(T_1-T_3)/(T_1-T_0)$. The correction circuit 30 corrects the object data 8 by using the weighted pre- and post-offset data (the pre-offset data 7 and the post-offset data 9). Note that weighting to be performed is not limited to the above linear weighting and may be nonlinear weighting.

(Effects)

According to Example 1 of the X-ray computed tomography apparatus 1 according to the embodiment, the following effects can be obtained.

The X-ray computed tomography apparatus 1 according to the embodiment includes the data acquisition circuit 25 (data acquisition unit) and the correction circuit 30 (processing unit). The data acquisition circuit 25 acquires data corresponding to outputs from the X-ray detector 24 (radiation detector). The correction circuit 30 executes correction processing for the object data 8 (third data), acquired by the data acquisition circuit 25 in actual scanning, based on at least one of the pre-offset data 7 (first data) acquired by the data acquisition circuit 25 before the actual scanning and the post-offset data 9 (second data) acquired by the data acquisition circuit 25 after the actual scanning.

In particular, the correction circuit 30 executes, for each of the pre-offset data 7 and the post-offset data 9, weighting processing corresponding to the ratio between the elapsed time indicating the time from the start time of actual scanning to a predetermined time in the actual scanning and the remaining time indicating the time from the predetermined time in the actual scanning to the end time of the actual scanning, and executes correction processing of correcting the object data 8 based on the pre-offset data 7 and the post-offset data 9 having undergone the weighting processing.

This makes it possible to properly obtain offset data again by using pre- and post-offset data (the pre-offset data 7 and the post-offset data 9) even when performing scanning accompanied by long-time imaging without allowing to use any quiescent time such as shuttle helical scanning, thereby suppressing artifacts originating from offset drifts.

EXAMPLE 2

Example 2 concerning the multi-offset correcting function of the X-ray computed tomography apparatus 1 according to the embodiment will be described below. Example 2 can implement correction with a cost lower than that in Example 1. In particular, Example 2 is preferably applied to a case in which the time taken for actual scanning is shorter than in Example 1. Note, however, that this is merely an example and not exhaustive.

Figure 4:
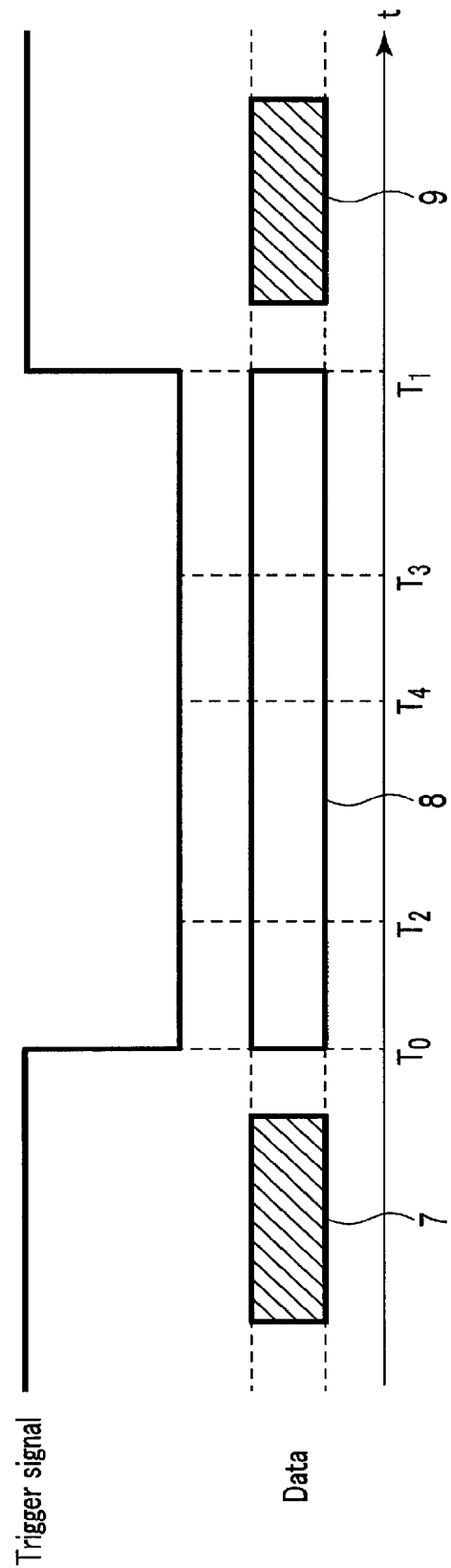
FIG. 4 is a diagram showing Example 2 in the X-ray computed tomography apparatus according to the embodiment.

FIG. 4 is a diagram (a graph representing temporal changes in various types of values/time series) showing Example 2 in the X-ray computed tomography apparatus 1 according to the embodiment.

The abscissa represents time t. FIG. 4 shows times $T_0$, $T_1$, $T_2$, $T_3$, and $T_4$. Assume that $T_4$ is a value satisfying $T_4=(T_0+T_1)/2$.

Figure 5:
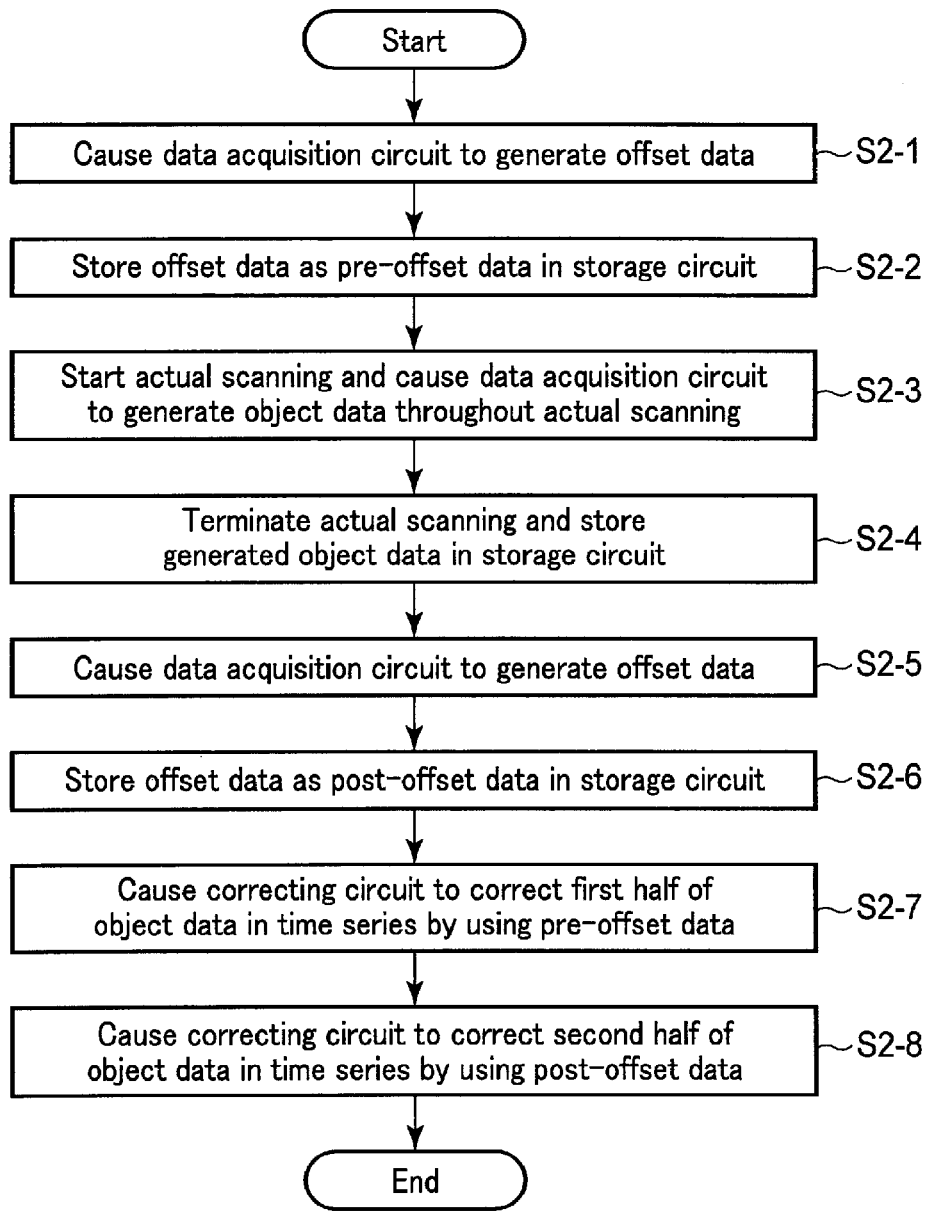
FIG. 5 is a flowchart showing Example 2 in the X-ray computed tomography apparatus according to the embodiment.

FIG. 5 is a flowchart showing Example 2 in the X-ray computed tomography apparatus 1 according to the embodiment. Example 2 will be described below in accordance with each step in the flowchart of FIG. 5.

(Step S2-1)

Before the execution of actual scanning (that is, $t<T_0$), the data acquisition circuit 25 generates offset data as data originating from dark currents in a period during which the X-ray tube 23 emits no X-rays (proceeding to step S2-2).
(Step S2-2)
The offset data generated in step S2-1 is stored as the pre-offset data 7 in the storage circuit 4 (proceeding to step S2-3).
(Step S2-3)
When the X-ray tube 23 starts emitting X-rays upon switching from trigger signal=High to trigger signal=Low at $t=T_0$, actual scanning starts. The data acquisition circuit 25 generates object data throughout the actual scanning (proceeding to step S2-4).
(Step S2-4)
When the X-ray tube 23 stops emitting X-rays upon switching from trigger signal=Low to trigger signal=High at $t=T_1$, the actual scanning ends. The generated object data is stored as the object data 8 in the storage circuit 4 (proceeding to step S2-5).
(Step S2-5)
The data acquisition circuit 25 generates offset data again as data originating from dark currents in a period during which the X-ray tube 23 emits no X-rays after the execution of the actual scanning (i.e., $t>T_1$) (proceeding to step S2-6).
(Step S2-6)
The offset data generated in step S2-5 is stored as the post-offset data 9 in the storage circuit 4 (proceeding to step S2-7).
(Step S2-7)
The object data 8 at $T_0 \leq t \leq T_4$ ($T_0 \leq t < T_4$: e.g., $t=T_2$) is corrected by the correction circuit 30 using the pre-offset data 7 (proceeding to step S2-8).
(Step S2-8)
The object data 8 at $T_4 < t \leq T_1$ ($T_4 \leq t \leq T_1$: e.g., $t=T_3$) is corrected by the correction circuit 30 using the post-offset data 9 (the procedure end).
(Effects)
According to Example 2 of the X-ray computed tomography apparatus 1 according to the embodiment, the following effects can be obtained.

The X-ray computed tomography apparatus 1 according to the embodiment includes the data acquisition circuit 25 (data acquisition unit) and the correction circuit 30 (processing unit). The data acquisition circuit 25 acquires data corresponding to outputs from the X-ray detector 24 (radiation detector). The correction circuit 30 executes correction processing for the object data 8 (third data), acquired by the data acquisition circuit 25 in actual scanning, based on at least one of the pre-offset data 7 (first data) acquired by the data acquisition circuit 25 before the actual scanning and the post-offset data 9 (second data) acquired by the data acquisition circuit 25 after the actual scanning.

In particular, the correction circuit 30 corrects the object data 8 based on the pre-offset data 7 when the elapsed time indicating the time from the start time of actual scanning to a predetermined time in the actual scanning is almost equal to or shorter than the remaining time indicating the time from the predetermined time in the actual scanning to the end time of the actual scanning, and corrects the object data 8 based on the post-offset data 9 when the elapsed time is longer than or almost equal to the remaining time.

This makes it possible to decrease the calculation cost as compared with Example 1 and properly obtain offset data again by using pre- and post-offset data (the pre-offset data 7 and the post-offset data 9) even when performing scanning accompanied by long-time imaging without allowing to use any quiescent time such as shuttle helical scanning, thereby suppressing artifacts originating from offset drifts.

EXAMPLE 3

Example 3 concerning the multi-offset correcting function of the X-ray computed tomography apparatus 1 according to the embodiment will be described below. Example 3 has a function of determining, based on the scanning time taken for actual scanning and a predetermined threshold, whether to execute the multi-offset correcting function according to Example 1. The predetermined threshold corresponds to, for example, a time based on which it is determined that a change in the temperature of the X-ray detector 24 is small during the execution of actual scanning.

FIGS. 6A and 6B are diagrams (graphs representing temporal changes in various types of values/time series) showing Example 3 in the X-ray computed tomography apparatus 1 according to the embodiment.

The abscissa represents time t. FIGS. 6A and 6B each show times $T_0$, $T_1$, and $T_5$. Note that FIG. 6A shows a case in which $T_1 > T_5$, and FIG. 6B shows a case in which $T_1 < T_5$.

Figure 7:
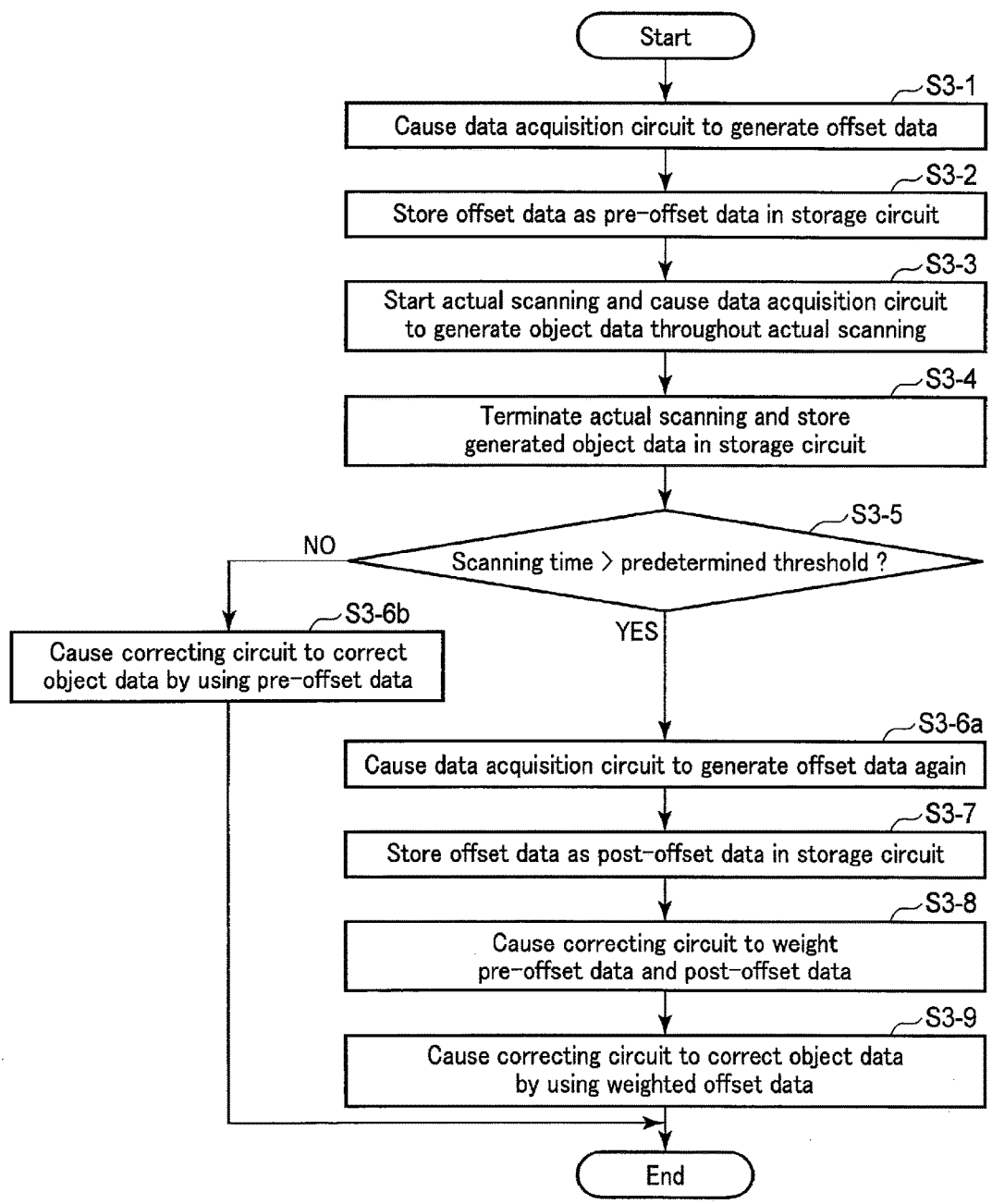
FIG. 7 is a flowchart showing Example 3 in the X-ray computed tomography apparatus according to the embodiment.

FIG. 7 is a flowchart showing Example 3 in the X-ray computed tomography apparatus 1 according to the embodiment. Example 3 will be described below in accordance with each step in the flowchart of FIG. 7.
(Step S3-1)
Before the execution of actual scanning (that is, $t<T_0$), the data acquisition circuit 25 generates offset data as data originating from dark currents in a period during which the X-ray tube 23 emits no X-rays (proceeding to step S3-2).
(Step S3-2)
The offset data generated in step S3-1 is stored as the pre-offset data 7 in the storage circuit 4 (proceeding to step S3-3).
(Step S3-3)
When the X-ray tube 23 starts emitting X-rays upon switching from trigger signal=High to trigger signal=Low at $t=T_0$, actual scanning starts. The data acquisition circuit 25 generates object data throughout the actual scanning (proceeding to step S3-4).
(Step S3-4)
When the X-ray tube 23 stops emitting X-rays upon switching from trigger signal=Low to trigger signal=High at $t=T_1$, the actual scanning ends. The generated object data is stored as the object data 8 in the storage circuit 4 (step S3-5).
(Step S3-5)
After the execution of the actual scanning (i.e., $t>T_1$), the control circuit 6 reads out a predetermined program stored in the storage circuit 4, and the program compares $T_1$ with the threshold $T_5$ (processing to step S3-6a or step S3-6b).
(Step S3-6a)
If it is determined in step S3-5 that $T_1 > T_5$ (or $T_1 \geq T_5$) as shown in FIG. 6A, the data acquisition circuit 25 generates offset data again as data originating from dark currents in a period during which the X-ray tube 23 emits no X-rays (proceeding to step S3-7).
(Step S3-6b)
If it is determined in step S3-5 that $T_1 < T_5$ (or $T_1 \leq T_5$) as shown in FIG. 6B, the multi-offset correcting function is not executed (stopped). That is, the correction circuit 30 corrects the object data 8 by using the pre-offset data 7 (the procedure end).
(Step S3-7)
The offset data generated in step S3-6a is stored as the post-offset data 9 in the storage circuit 4 (proceeding to step S3-8).
(Step S3-8)
The correction circuit 30 assigns weights to the pre-offset data 7 and the post-offset data 9 in accordance with the ratio of the elapsed time of object scanning to the total time of the object scanning and the ratio of the remaining time of the object scanning to the total time of the object scanning (proceeding to step S3-9).
(Step S3-9)

The correction circuit 30 corrects the object data 8 by using the weighted pre- and post-offset data (the pre-offset data 7 and the post-offset data 9) (the procedure end).

Example 3 has a function of determining, based on the scanning time taken for actual scanning and a predetermined threshold, whether to execute the multi-offset correcting function according to "Example 1".

In association with this function, Example 3 may be implemented so as to have a function of determining, based on the scanning time taken for actual scanning and a predetermined threshold, whether to execute the multi-offset correcting function according to "Example 2".

Alternatively, Example 3 may be implemented so as to have a function of determining by using, for example, two different thresholds whether to execute the multi-offset correcting function according to "Example 1", the multi-offset correcting function according to "Example 2", or neither of the functions.

In addition, Example 3 may be implemented such that an operator such as a doctor determines in advance whether to execute the multi-offset correcting function, when setting a scan sequence (before the start of an actual scan sequence). In other words, Example 3 may be implemented such that an operator such as a doctor determines in advance whether to obtain the post-offset data 9, when setting a scan sequence (before the start of an actual scan sequence).
(Effects)

According to Example 3 of the X-ray computed tomography apparatus 1 according to the embodiment, the following effects can be obtained.

The X-ray computed tomography apparatus 1 according to the embodiment includes the data acquisition circuit 25 (data acquisition unit) and the correction circuit 30 (processing unit). The data acquisition circuit 25 acquires data corresponding to outputs from the X-ray detector 24 (radiation detector). The correction circuit 30 executes correction processing for the object data 8 (third data), acquired by the data acquisition circuit 25 in actual scanning, based on at least one of the pre-offset data 7 (first data) acquired by the data acquisition circuit 25 before the actual scanning and the post-offset data 9 (second data) acquired by the data acquisition circuit 25 after the actual scanning.

In particular, when the execution time $T_1$ of actual scanning is almost equal to or shorter than the threshold $T_5$, the data acquisition circuit 25 stops acquiring the post-offset data 9, and the correction circuit 30 corrects the object data 8 based on the pre-offset data 7.

This makes it possible to properly determine a case in which pre- and post-offset data (the pre-offset data 7 and the post-offset data 9) should be used (when performing scanning accompanied by long-time imaging without allowing to use any quiescent time, such as shuttle helical scanning) or a case in which there is no need to use pre- and post-offset data (the pre-offset data 7 and the post-offset data 9) because of a short actual scanning time. In addition, it is possible to obtain offset data again and suppress artifacts originating from offset drifts.
[Modification]

The X-ray computed tomography apparatus 1 according to the embodiment includes the correction circuit 30. In addition, the correction circuit 30 executes the multi-offset correcting function described in Examples described above.

However, the X-ray computed tomography apparatus 1 may not include the correction circuit 30 and execute the multi-offset correcting function by using another constituent element. For example, in a modification, the image processing circuit 32 of the X-ray computed tomography apparatus 1 may execute the multi-offset correcting function. In another modification, the control circuit 6 of the X-ray computed tomography apparatus 1 may execute the multi-offset correcting function by reading out a predetermined program stored in the storage circuit 4.

The X-ray computed tomography apparatus 1 according to the embodiment includes the correction circuit 30. In addition, the correction circuit 30 corrects the object data 8 based on offset data (the pre-offset data 7 and the post-offset data 9). On the other hand, before the correction circuit 30 executes the multi-offset correcting function, the reconstruction circuit 31 may reconstruct offset data (the pre-offset data 7 and the post-offset data 9) and the object data 8 into volume data. In this case, the correction circuit 30 corrects the volume data reconstructed from the object data 8 based on the offset data (the pre-offset data 7 and the post-offset data 9) and the reconstructed volume data.

The multi-offset correcting function of the X-ray computed tomography apparatus 1 according to the embodiment is not limited to the one using two offset data (the pre-offset data 7 and the post-offset data 9). For example, the data acquisition circuit 25 may obtain "intermediate offset data" by setting a predetermined quiescent time in part of the obtaining time of the object data 8, and the correction circuit 30 may then correct the object data 8 by using the three offset data. Likewise, the data acquisition circuit 25 may obtain four or more offset data, and the correction circuit 30 may then correct the object data 8 by using the four or more offset data.

The functions (the multi-offset correcting function and the like) of the X-ray computed tomography apparatus 1 according to the embodiment are not limited to the X-ray computed tomography apparatus 1. For example, the functions may be executed by other types of radiation medical imaging diagnostic apparatus typified by an X-ray diagnostic apparatus, a single photon emission tomography (SPECT) apparatus, a positron tomography (PET) apparatus, and the like.

In addition, the functions (the multi-offset correcting function and the like) of the X-ray computed tomography apparatus 1 according to the embodiment may be implemented by installing programs for executing data set compression processing in a computer such as a workstation and loading them in the memory. In this case, the programs which can cause the computer to execute the above method can be distributed by being stored in storage media such as magnetic disks (Floppy® disks, hard disks, and the like), optical disks (CD-ROMs, DVD-ROMs, and the like), and semiconductor memories.

Each component of the above embodiment is implemented by at least properly and mainly combining a circuit, circuitry, processor, memory, and the like.

The word "processor" means a circuit such as a CPU (Central Processing Unit), GPU (Graphics Processing Unit), ASIC (Application Specific Integrated Circuit), programmable logic device (e.g., an SPLD (Simple Programmable Logic Device), a CPLD (Complex Programmable Logic Device), or an FPGA (Field Programmable Gate Array)), or the like. The processor implements functions by reading out programs stored in the storage circuit and executing them. Note that it is possible to directly incorporate programs in the circuit of the processor instead of storing them in the storage circuit. In this case, the processor implements functions by reading out programs incorporated in the circuit and executing them. Note that each processor in this embodiment may be formed as one processor by combining a plurality of independent circuits to implement functions as well as being formed as a single circuit for each processor. In addition, a plurality of constituent elements may be integrated into one processor to implement its function.
(Effects)

According to the above embodiment, the following effects can be obtained.

The radiation medical imaging diagnostic apparatus according to the embodiment includes the data acquisition unit and the processing unit. The data acquisition unit acquires data corresponding to outputs from the radiation detector. The processing unit executes correction processing for the third data, acquired by the data acquisition unit in actual scanning, based on at least one of the first data acquired by the data acquisition unit before the actual scanning and the second data acquired by the data acquisition unit after the actual scanning.

This makes it possible to properly obtain offset data again by using pre- and post-offset data even when performing scanning accompanied by long-time imaging, thereby suppressing artifacts originating from offset drifts.

EXAMPLE 4

FIG. 8 is a block diagram showing an example of the arrangement of the X-ray computed tomography apparatus 1 according to Example 4. As shown in FIG. 8, the X-ray computed tomography apparatus 1 further includes a temperature measuring device 27 which measures a temperature associated with the X-ray detector 24.

The temperature measuring device 27 has a thermocouple and is provided in the data acquisition circuit 25. Note that the temperature measuring device 27 may be provided in the X-ray detector 24. A device which measures a temperature is not limited to a thermocouple. The temperature measuring device 27 measures a temperature associated with the X-ray detector 24 over time. A temperature associated with the X-ray detector 24 is, for example, the temperature of the data acquisition circuit 25 corresponding to each X-ray detection element. Note that a temperature associated with the X-ray detector 24 may be the temperature of each X-ray detection element. For example, the temperature measuring device 27 converts a measured temperature into the temperature of each X-ray detection element by using a predetermined conversion table. The temperature measuring device 27 outputs the data of the temperature of each X-ray detection element to a noncontact data transmission device 28.

The noncontact data transmission device 28 adds the data of the temperature corresponding to each X-ray detection element to the first data and the second data acquired by the data acquisition circuit 25, and transmits the resultant data to the correction circuit 30.

The storage circuit 4 stores the first weights to be assigned to the first data and the second weights to be assigned to the second data. For example, the storage circuit 4 stores the first correspondence table of the first weights corresponding to times in the total time of actual scanning concerning each of a plurality of temperature ranges and each of the X-ray detection elements. In addition, the storage circuit 4 stores the second correspondence table of the second weights corresponding to times in the total time of actual scanning concerning each of a plurality of the temperature ranges and each of the X-ray detection elements. The relationship between the times in the total time of actual scanning and the first weights in the first correspondence table and the relationship between the times in the total time of actual scanning and the second weights in the second correspondence table are symmetrical to each other with respect to the average value (e.g., 0.5) of the first and second weights, and are linear or nonlinear relationships. A nonlinear relationship is represented by, for example, a logistic curve, quadratic function, cubic function, or exponential function. These relationships are set in advance by characteristics representing the magnitudes of dark currents corresponding to the temperatures of the data acquisition circuit 25 and the respective X-ray detection elements.

Note that the storage circuit 4 may store a mathematical expression for calculating the second weight by subtracting the first weight from 1. Alternatively, the storage circuit 4 may store a mathematical expression for calculating the first and second weights for each X-ray detection element based on temperatures and a time in the total time of actual scanning, in place of the first and second correspondence tables.

The correction circuit 30 decides the first and second weights based on measured temperatures. For example, the correction circuit 30 decides the first weight based on a measured temperature, the measurement time of the temperature, and the first correspondence table, and decides the second weight based on a measured temperature, the measurement time of the temperature, and the second correspondence table. The correction circuit 30 executes weighting processing for the first data by assigning the first data with the first weight decided for each X-ray detection element. The correction circuit 30 executes weighting processing for the second data by assigning the second data with the second weight decided for each X-ray detection element. The correction circuit 30 corrects the third data by executing the multi-offset correcting function using the first data assigned with the first weight and the second data assigned with the second weight.
(Operation)

The operation of Example 4 is the operation of deciding the first and second weights based on temperatures and correcting the third data. A processing procedure associated with the operation of Example 4 will be described below.

Figure 10:
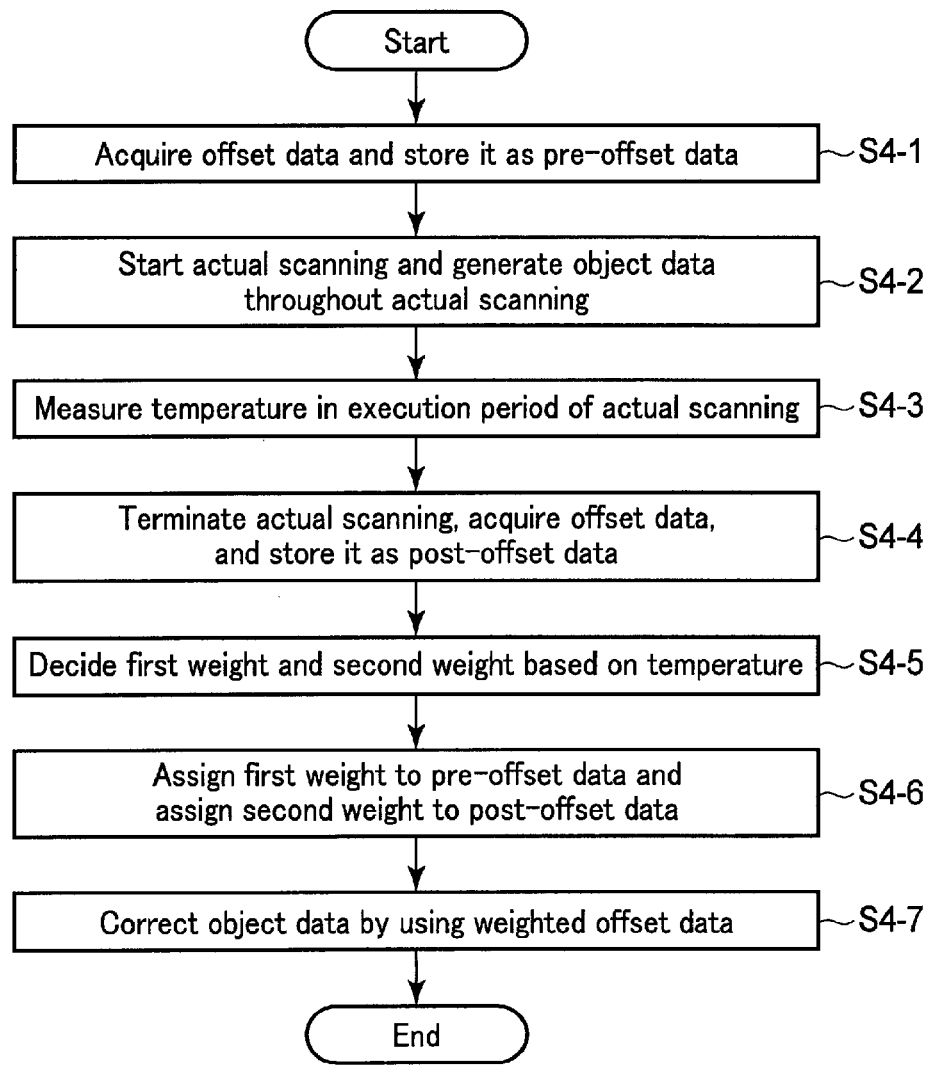
FIG. 10 is a flowchart showing an example of a processing procedure in the X-ray computed tomography apparatus according to Example 4.

FIG. 10 is a flowchart showing a processing procedure associated with the operation of Example 4.
(Step S4-1)

Before the execution of actual scanning, offset data is acquired. The acquired offset is stored as pre-offset data in the storage circuit 4 (proceeding to step S4-2).
(Step S4-2)

When the X-ray tube 23 starts emitting X-rays upon switching from trigger signal=High to trigger signal=Low at $t=T_0$, actual scanning starts. Object data is generated throughout the actual scanning. The generated object data is stored in the storage circuit 4 (proceeding to step S4-3).
(Step S4-3)

In the execution period of actual scanning, temperatures are measured. The measured temperatures are stored in the storage circuit 4 (proceeding to step S4-4). That is, the temperatures of the X-ray detection elements are monitored during the actual scanning. When switching occurs from trigger signal=Low to trigger signal=High at $t=T_1$, the X-ray tube 23 stops emitting X-rays, and the actual scanning ends.
(Step S4-4)

The data acquisition circuit 25 generates offset data again as data originating from dark currents in a period during which the X-ray tube 23 emits no X-rays after the execution of the actual scanning (i.e., $t>T_1$). The generated offset data is stored as post-offset data in the storage circuit 4 (proceeding to step S4-5).

(Step S4-5)

The first and second weights are decided based on measured temperatures (proceeding to step S4-6). More specifically, the correction circuit 30 specifies a temperature range including the measured temperatures. The correction circuit 30 then decides the first weight by using the first correspondence table corresponding to the specified temperature range and the measurement time of a temperature in the actual scanning. The correction circuit 30 also decides the second weight by using the second correspondence table corresponding to the specified temperature range and the measurement time of a temperature in the actual scanning.

Figure 9:
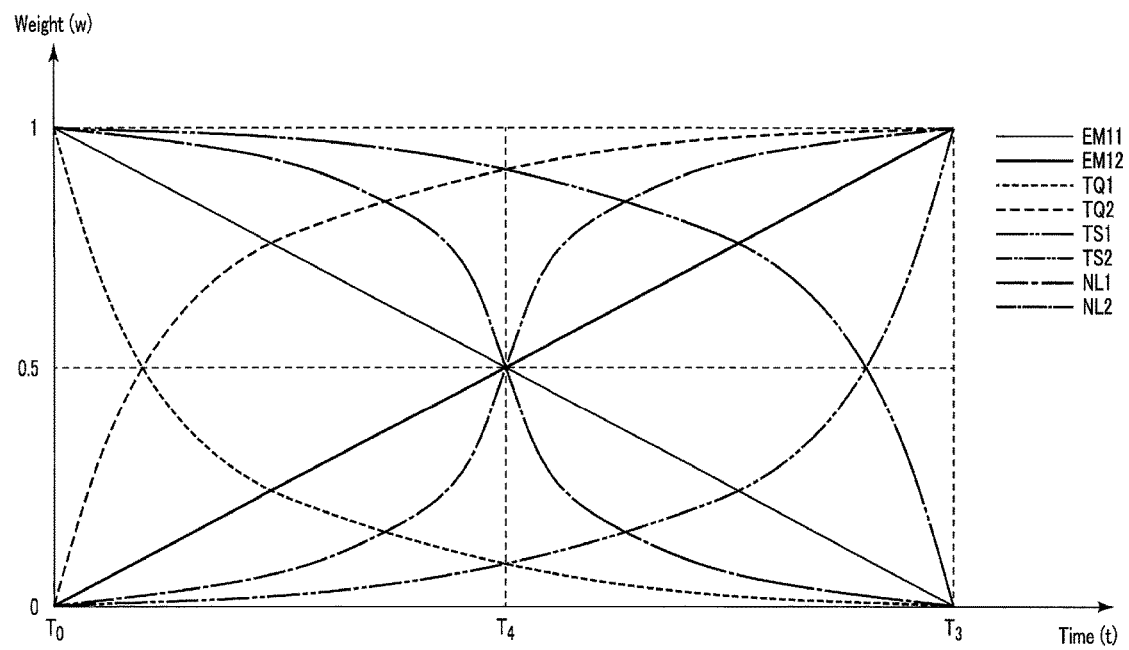
FIG. 9 is a graph showing an example of change in weight in the X-ray computed tomography apparatus according to Example 4.

FIG. 9 is a graph showing a relationship indicating the first weights corresponding to times and a relationship indicating the second weights corresponding to times for each temperature in a given X-ray detection element. A straight line EM11 represents the linear first weight as in Example 1, and a straight line EM12 represents the linear second weight as in Example 1. Curves NL1, TS1, and TQ1 represent changes in the first weight with time, and curves NL2, TS2, and TQ2 represent changes in the second weight with time. The curves NL1 and NL2 each represent a logistic curve or cubic curve showing an example of a nonlinear weight change in Example 1. The curves TS1, TS2, TQ1, and TQ2 in FIG. 9 each represent an exponential function or quadratic function showing an example of a nonlinear weight change in Example 1.

The shapes of the respective types of curves and the straight lines shown in FIG. 9 depend on the above characteristics in the data acquisition circuit 25 and the respective X-ray detection elements. For this reason, the shape of each curve showing the above relationship in FIG. 9 is an example, and a change in weight with time is not limited to any of the curve shapes shown in FIG. 9. FIG. 9 shows the six curves and the two straight lines. However, the numbers of curves and straight lines are not limited to them.

For example, when deciding a weight corresponding to a temperature, the correction circuit 30 selects one of pairs of the curve TS1 and TS2, the curves NL1 and NL2, the straight lines EM11 and EM12, and the curves TQ1 and TQ2.

(Step S4-6)

In weighting processing, the first weight is assigned to the pre-offset data. In addition, the second weight is assigned to the post-offset data (processing to step S4-7). As shown in FIG. 9, weights are assigned in accordance with times in the actual scanning.

(Step S4-7)

The correction circuit 30 corrects the object data 8 by using the weighted pre- and post-offset data (the pre-offset data 7 and the post-offset data 9) (the procedure end).

(Effects)

According to the X-ray computed tomography apparatus 1 of Example 4, the following effects can be obtained.

The X-ray computed tomography apparatus 1 decides the first and second weights to be respectively assigned to the pre-offset data and the post-offset data used for offset correction based on temperatures associated with the X-ray detector 24. That is, according to Example 4, it is possible to decide proper weights to be respectively assigned to pre-offset data and post-offset data in accordance with the temperature of each X-ray detection element.

For example, a dark current in an X-ray detection element immediately after actual scanning is a value corresponding to a room temperature. Since the temperature of the X-ray detection element rises in accordance with the elapsed time of the actual scanning, the dark current relatively increases. For this reason, according to Example 4, in an example with a long scanning time, in particular, weights can be optimized in accordance with temperatures associated with the X-ray detector 24, and the accuracy of offset correction for object data can be further improved. As described above, according to Example 4, artifacts caused by offset drifts can be further reduced.

[Modification]

This modification differs from Example 4 in that the first and second weights are decided based on temperatures and the use period of the X-ray detector.

The storage circuit 4 stores the use period of the X-ray detector 24 from the start time of the use of the X-ray computed tomography apparatus 1 (e.g., the time of installation in a medical institution) to the current time point. The storage circuit 4 stores the first and second correspondence tables corresponding to each of a plurality of temperature ranges and each of the plurality of use ranges of the respective X-ray detection elements. A use range corresponds to a period for specifying the first and second correspondence tables in accordance with a use period, and is defined by, for example, a year and a month. That is, a use range is used to specify a curve representing a change in weight as shown in FIG. 9, which corresponds to a temperature in accordance with a use period. Note that the storage circuit 4 may store a mathematical expression for calculating the first and second weights corresponding to each X-ray detection element by using a use period, temperatures, and above characteristics.

The correction circuit 30 decides the first and second weights based on temperatures and a use period. More specifically, the correction circuit 30 specifies a use range including a use period. The correction circuit 30 then decides the first weight by using the first correspondence table corresponding to the specified use range and the specified temperature range and the measurement times of temperatures in this actual scanning. The correction circuit 30 also decides the second weight by using the second correspondence table corresponding to the specified use range and the specified temperature range and the measurement times of temperatures in this actual scanning.

(Effects)

According to the X-ray computed tomography apparatus 1 of this modification, the following effects can be obtained.

The X-ray computed tomography apparatus 1 according to this modification can decide the first and second weights to be respectively assigned to pre-offset data and post-offset data used for offset correction based on temperatures associated with the X-ray detector 24 and a use period, and correct object data by using the weighed pre- and post-offset data. That is, according to the modification, it is possible to decide proper weights to be respectively assigned to pre-offset data and post-offset data in accordance with the temperature of each X-ray detection element and the use period of the X-ray detector 24.

As the semiconductor characteristics and the like of the X-ray detector 24 change in accordance with the use period of the X-ray computed tomography apparatus 1 according to this modification, and hence the dependence of a weight corresponding to the temperature of the X-ray detector 24 changes. For this reason, according to this modification, it is possible to optimize weights in accordance with the use period of the X-ray detector 24 and temperatures associated with the X-ray detector 24. This can improve the accuracy of offset correction with respect to object data. As described above, according to this modification, it is possible to further reduce artifacts caused by offset drifts.

The X-ray computed tomography apparatus 1 and the radiation medical imaging diagnostic apparatus described above can suppress the occurrence of artifacts in long-time imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X ray computed tomography apparatus, comprising:
   an X ray tube configured to generate X rays;
   an X ray detector configured to detect the X rays;
   a data acquisition circuit configured to acquire data corresponding to an output from the X ray detector; and
   a correction circuit configured to execute correction processing for third data acquired by the data acquisition circuit in actual scanning, based on first data acquired by the data acquisition circuit in a state of non-irradiation with X rays before the actual scanning and second data acquired by the data acquisition circuit in the state of non-irradiation with X rays after the actual scanning,
   wherein the correction circuit is further configured to execute, for each of the first data and the second data, weighting processing corresponding to a ratio between an elapsed time indicating a time from a start time of the actual scanning to a predetermined time and a remaining time indicating a time from the predetermined time to an end time of the actual scanning, and
   execute the correction processing based on the first data and the second data for which the weighting processing has been executed.

2. The apparatus according to claim 1, wherein the first data and the second data are offset data obtained from the X ray detector in the state of non-irradiation with X rays, and
   the correction circuit is further configured to execute offset correction as the correction processing for the third data.

3. The apparatus according to claim 1, wherein the correction circuit is further configured to correct the third data based on the first data when the elapsed time indicating the time from the start time of the actual scanning to the predetermined time is shorter than the remaining time indicating the time from the predetermined time to the end time of the actual scanning, and
   correct the third data based on the second data when the elapsed time is longer than the remaining time.

4. The apparatus according to claim 1, wherein the data acquisition circuit is further configured to stop acquiring the second data when an execution time of the actual scanning is not more than a predetermined value, and
   the correction circuit is further configured to correct the third data based on the first data.

5. The apparatus according to claim 1, wherein the correction circuit is further configured to execute the correction processing by using a data set acquired for each view by the data acquisition circuit as at least one of the first data and the second data.

6. The apparatus according to claim 5, wherein the correction circuit is further configured to execute the correction processing by averaging the data set.

7. The apparatus according to claim 1, further comprising a temperature measuring device configured to measure a temperature associated with the X ray detector,
   wherein the correction circuit is further configured to decide a first weight to be assigned to the first data and a second weight to be assigned to the second data based on the measured temperature, and
   execute the correction processing by using the first data assigned with the first weight and the second data assigned with the second weight.

8. The apparatus according to claim 7, wherein a relationship between a time in a total time of the actual scanning and the first weight and a relationship between a time in the total time and the second weight are symmetrical with respect to an average value of the first weight and the second weight, and are nonlinear relationships.

9. The apparatus according to claim 7, wherein the correction circuit is further configured to decide the first weight and the second weight based on the measured temperature and a use period of the X ray detector.

10. An X-ray radiation medical imaging diagnostic apparatus comprising:
    an X-ray radiation detector configured to detect X-ray radiation; and
    a correction circuit configured to execute correction processing for third data detected by the X-ray radiation detector in actual imaging based on first data detected by the X-ray radiation detector in a state of non-irradiation with X-ray radiation before the actual imaging and second data detected by the X-ray radiation detector in actual imaging based on second data detected by the X-ray radiation detector in the state of non-irradiation with X-ray radiation after the actual imaging,
    wherein the correction circuit is further configured to execute, for each of the first data and the second data, weighting processing corresponding to a ratio between an elapsed time indicating a time from a start time of the actual scanning to a predetermined time and a remaining time indicating a time from the predetermined time to an end time of the actual scanning, and
    execute the correction processing based on the first data and the second data for which the weighting processing has been executed.

* * * * *